(12) United States Patent
Meunier et al.

(10) Patent No.: US 8,652,461 B2
(45) Date of Patent: Feb. 18, 2014

(54) **BLOOD-CHOLESTEROL-LOWERING STRAIN OF *LACTOBACILLUS DELBRUECKII***

(75) Inventors: Agnès Meunier, Limeil-Brévannes (FR); Florent Lalanne, St Didier de Formans (FR); Catherine Nicolle, Gif sur Yvette (FR); Artem Khlebnikov, New Rochelle, NY (US); Christèle Gaye, Vincennes (FR)

(73) Assignee: Campagnie Gervais Danone, Paris (FR)

( * ) Notice: Subject to any disclaimer, the term of this patent is extended or adjusted under 35 U.S.C. 154(b) by 20 days.

(21) Appl. No.: 13/129,255

(22) PCT Filed: Nov. 19, 2009

(86) PCT No.: PCT/IB2009/007681
§ 371 (c)(1),
(2), (4) Date: Jul. 19, 2011

(87) PCT Pub. No.: WO2010/058294
PCT Pub. Date: May 27, 2010

(65) Prior Publication Data
US 2011/0305679 A1     Dec. 15, 2011

(30) Foreign Application Priority Data
Nov. 19, 2008 (FR) .................................. 08 06467

(51) Int. Cl.
*A01N 63/00* (2006.01)
*C12N 1/20* (2006.01)

(52) U.S. Cl.
USPC ..................... 424/93.45; 435/252.9; 435/853

(58) Field of Classification Search
None
See application file for complete search history.

(56) References Cited

PUBLICATIONS

Bergy's Manual of Systematic Bacteriology. 1986, vol. 2, pp. 1220, 1222 and 1223.*
Akalin. Influence of Yogurt and Acidophilus Yogurt on Serum Cholesterol Levels in Mice, J Dairy Sci., 80, 2721-2725, 1997.
Tamai, Effects of Milk Fermented by Culturing with Various Lactic Acid Bacteria and a Yeast on Serum Cholesterol Level in Rats, Journal of Fermentation and Bioengineering, 81, 181-182, 1996.
Terahara, Preventive Effect of *Lactobacillus delbrueckii* Subsp. Bulgaricus on the Oxidation of LDL, Biosci. Biotechnol. Biochem., 64, 1868-1873, 2000.
Portugal, Effect of *Lactobacillus delbrueckii* on Cholesterol Metabolism in Germ-Free Mice and on Atherogenesis in Apolipoprotein E Knock-Out Mice, Brazilian Journal of Medical and Biological Research, 37, 629-635, 2006.

* cited by examiner

*Primary Examiner* — Vera Afremova
(74) *Attorney, Agent, or Firm* — Morgan, Lewis & Bockius LLP

(57) ABSTRACT

The invention relates to a novel strain of *Lactobacillus delbrueckii* having blood-cholesterol-lowering properties, and to the use thereof for the manufacture of blood-cholesterol-lowering fermented products, in particular of milk products.

7 Claims, 3 Drawing Sheets

BLOOD-CHOLESTEROL-LOWERING STRAIN OF *LACTOBACILLUS DELBRUECKII*

RELATED APPLICATIONS

Figure 1:
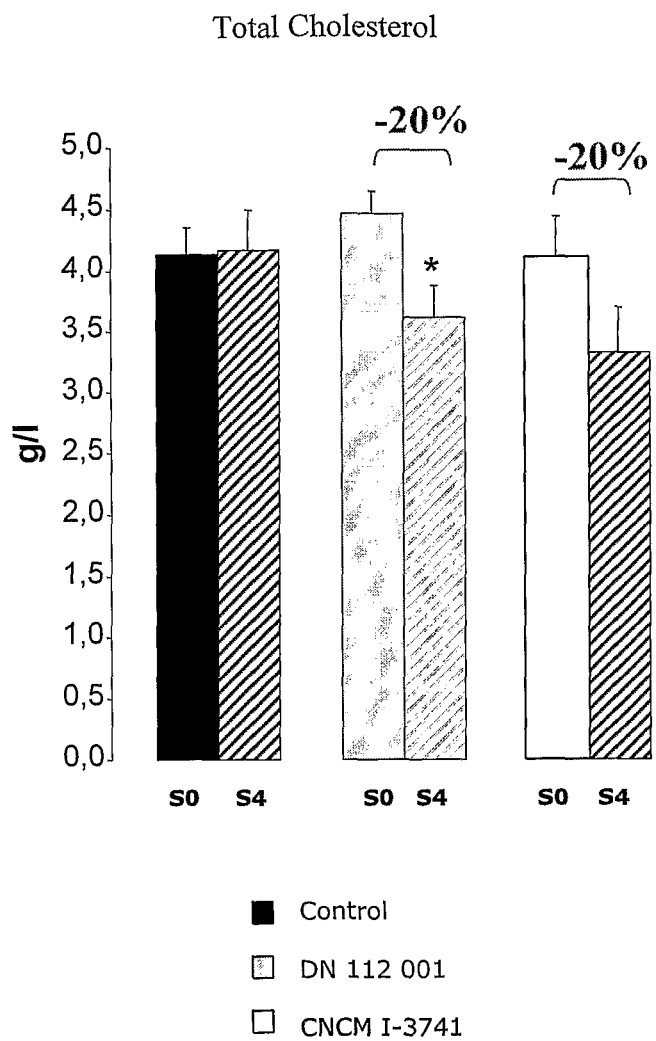

The present application is a U.S. National Phase Application of International Application No. PCT/IB2009/007681 (filed Nov. 19, 2009) which claims priority to French Application No. 0806467 (filed Nov. 19, 2008) which are hereby incorporated by reference in their entirety.

The invention relates to a novel strain of *Lactobacillus delbrueckii* having blood-cholesterol-lowering properties.

It has been reported that certain fermented milk products can exert blood-cholesterol-lowering effects. These effects depend in particular on the presence, in these products, of specific strains of lactic acid bacteria, belonging to certain given species. They are in particular strains of enterococci, such as *Enterococcus faecium* (Application EP0101209) or *Enterococcus mundtii* (PCT Application WO 2007/108583), of bifidobacteria (PCT Application WO 2007/029773) (Xiao et al., J Dairy Sci, 86, 2452-61, 2003), and of lactobacilli.

Among the lactobacilli, blood-cholesterol-lowering strains have been identified only in a few species, such as *Lactobacillus casei* (Brashears et al., J Dairy Sci, 81, 2103-10, 1998; Kapila & Sinha, Indian J Med Sci, 60, 361-70, 2006; Kawase et al., J Dairy Sci, 83, 255-63, 2000), *Lactobacillus fermentum* (Gilliland & Walker, J Dairy Sci, 73, 905-11, 1990; Pereira et al., Appl Environ Microbiol, 69, 4743-52, 2003), and especially *Lactobacillus acidophilus* (Gilliland et al., Appl Environ Microbiol, 49, 377-81, 1985; Lin et al., J Dairy Sci, 72, 2885-99, 1989; Gilliland & Walker, J Dairy Sci, 73, 905-11, 1990; Gupta et al., Int J Food Microbiol, 29, 105-9, 1996; Anderson & Gilliland, J Am Coll Nutr, 18, 43-50, 1999).

On the other hand, other species of lactobacilli, and in particular *Lactobacillus delbrueckii*, which is one of the species most widely used in the manufacture of fermented milk products since it constitutes, in combination with *Streptococcus thermophiles*, the conventional "yoghurt symbiosis", was until now considered to be devoid of blood-cholesterol-lowering effects.

Thus, it was shown that conventional yoghurts (obtained by fermentation with *Lactobacillus delbrueckii*+*Streptococcus thermophiles*) did not have the blood-cholesterol-lowering effects of milk products obtained by fermentation with *Lactobacillus acidophilus* and *Streptococcus thermophiles* (Akalin et al., J Dairy Sci, 80, 2721-5, 1997), or with *Bifidobacterium longum* (Xiao et al., J Dairy Sci, 86, 2452-61, 2003). It was also reported that the administration of *Lactobacillus delbrueckii* to axenic mice induced a decrease in fecal cholesterol excretion, but no change in the level of blood or hepatic cholesterol. When *Lactobacillus delbrueckii* was administered to mice deficient in apolipoprotein E (ApoE KO mice), no effect was observed, whether for fecal, hepatic or blood cholesterol (Portugal et al., Braz J Med Biol Res, 39, 629-35, 2006).

The inventors have now isolated a strain of *Lactobacillus delbrueckii* which, surprisingly, has blood-cholesterol-lowering properties. This strain also has the capacity for growth on milk and the propagation capacity of the *Lactobacillus delbrueckii* strains conventionally used in the manufacture of yoghurts, and can therefore be conveniently used in the manufacture of fermented milk products, and in particular of yoghurts.

Accordingly, the present invention provides the *Lactobacillus delbrueckii* subspecies lactis strain deposited on 6 Apr. 2007 under number I-3741 with the CNCM (Collection Nationale de Cultures de Microorganismes) [French National Microorganism Culture Collection], 25 rue du Docteur Roux, in Paris.

The characteristics of this strain are the following:
Morphology: Gram-positive microorganism, more or less long, granular bacilli which are quite small.
Fermentation of the following sugars (results obtained on an API 50 CH strip—API MRS medium at 37° C. for 48 h): D-glucose, D-fructose, D-mannose, N-acetylglucosamine, maltose, lactose, sucrose, trehalose.

The present invention also provides a lactic ferment comprising the *Lactobacillus delbrueckii* subspecies lactis strain CNCM I-3741 combined with one or more other strain(s) of lactic acid bacteria.

Said other strain(s) may in particular belong to the following species: *Lactobacillus acidophilus*, *Lactobacillus plantarum*, *Lactobacillus casei* subsp. *casei*, *Lactobacillus casei* subsp. *rhamnosus*, *Lactobacillus zeae*, *Lactobacillus salivarius*, *Lactobacillus lactis*, *Lactobacillus helveticus*, *Lactobacillus casei*, *Lactobacillus paracasei*, *Lactobacillus cremoris*, *Lactobacillus rhamnosus*, *Lactobacillus gasseri*, *Lactobacillus delbrueckii* subsp. *bulgaricus*, *Lactobacillus delbrueckii* subsp. *lactis*, *Lactobacillus delbrueckii* subsp. *delbrueckii*, *Lactobacillus delbrueckii* subsp. *bulgaricus*, *Lactobacillus reuteri*, *Lactobacillus amylovorus*, *Lactobacillus crispatus*, *Lactobacillus curvatus*, *Lactobacillus johnsonii*, *Lactobacillus fermentum*, *Lactobacillus brevis*, *Streptococcus thermophilus*, *Lactococcus lactis* subsp. *lactis*, *Lactococcus lactis* subsp. *cremoris*, *Enterococcus faecium*, *Pediococcus pentosaceus*, *Pediococcus acidilactici*, *Bifidobacterium longum*, *Bifidobacterium breve*, *Bifidobacterium bifidum*, *Bifidobacterium infantis*, *Bifidobacterium lactis*, *Bifidobacterium animalis*, *Bifidobacterium animalis* sp. *lactis*, *Bifidobacterium infantis*, *Bifidobacterium adolescentis*.

According to one preferred embodiment of a lactic ferment in accordance with the present invention, the *Lactobacillus delbrueckii* subspecies lactis strain CNCM I-3741 is combined with at least one strain of *Lactobacillus delbrueckii bulgaricus* and at least one strain of *Streptococcus thermophilus*.

The present invention also provides a method for preparing a fermented product, which method is characterized in that it comprises the fermentation of a suitable medium with the CNCM I-3741 strain, or with a lactic ferment in accordance with the invention, containing said strain. According to one preferred embodiment of this method, the medium used for the fermentation is milk or a milk-based medium, or a plant juice (fruit and/or vegetable juice) or a mixture of these media.

The present invention also provides fermented products, in particular fermented milk products, containing bacteria of the CNCM I-3741 strain, and optionally bacteria of one or more other strains of lactic acid bacteria.

According to one preferred embodiment of a fermented product in accordance with the invention, it contains, after fermentation, at least $1\times10^6$ CFU (colony-forming units), preferably at least $1\times10^7$ CFU, and more preferably between $1\times10^7$ and $1\times10^9$ CFU, per ml of bacteria of the CNCM I-3741 strain.

The present invention also relates to the use of the CNCM I-3741 strain, or of lactic ferments or of fermented products containing said strain, for obtaining products which induce a decrease in the blood cholesterol level, in particular the LDL cholesterol level.

The present invention will be understood more clearly by means of the further description which follows, which refers to examples illustrating the blood-cholesterol-lowering properties of the CNCM I-3741 strain. It should be clearly understood, however, that these examples are given only by way of illustration of the subject of the invention, of which they in no way constitute a limitation.

EXAMPLE 1

In Vivo Blood-Cholesterol-Lowering Effect of the CNCM I-3741 Strain

The effect of the consumption of the CNCM I-3741 strain (also referred to hereinafter as DN 111 244), and, as a positive control, of the *Lactobacillus acidophilus* I-2273 strain described in patent EP1251860 (also hereinafter referred to as DN 112 001), was evaluated in vivo in mice deficient in apolipoprotein E (apoE KO). The I-2273 strain is a strain which has a blood-cholesterol-lowering activity in vitro, but which cannot be readily used for obtaining fermented milk products since it grows very poorly on milk.

The experimental protocol is the following:

Forty apoE KO mice, 9 to 10 weeks old, were divided up into 4 groups of 10 mice. These mice were provided by Charles River Laboratories, L'Arbresle (France).

All the mice received, for 28 days, a lipid-enriched diet supplemented, by gavage, with:
- 300 µl/day of a culture containing $6 \times 10^8$ CFU of the DN 111 244 strain, obtained under the culture conditions on milk-MRS medium (group 1);
- 300 µl/day of a culture containing $6 \times 10^8$ CFU of the DN 112 001 strain, obtained using the same culture conditions on milk-MRS medium as those described for the DN 111 244 strain (group 2);
- 300 µl/day of a control milk, the composition of which is the following: skimmed milk (control).

The DN 112 001 and DN 111 244 (CNCM I-3741) strains were cultured on MRS medium. They were subsequently resuspended in milk so as to obtain a milk containing $6 \times 10^8$ CFU of bacteria.

The daily intake of the animals in the three groups was identical. The animals were weighed at the beginning of the experiment, and then at 5-day intervals over the course of the treatment. No significant difference between the various groups was observed.

The total plasma cholesterol level and the LDL cholesterol level were measured at the beginning of the experiment, and after the 28 days of treatment.

Plasma Lipid Assay

Figure 2:
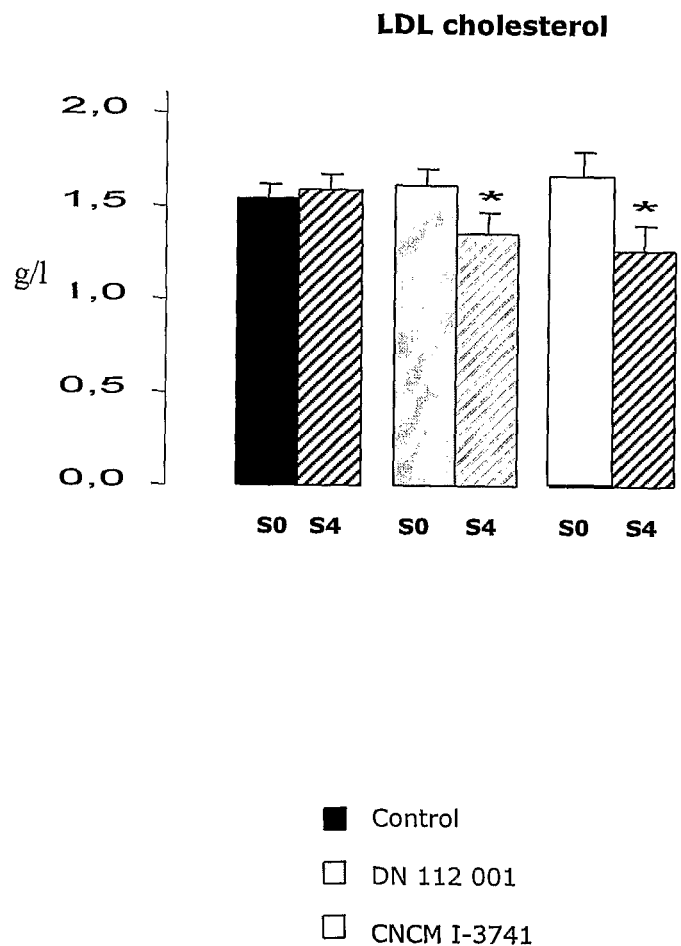

The results are shown in FIGS. 1 and 2.

These results show that, after the 28 days of treatment, a decrease in total cholesterol and in LDL cholesterol (the "bad" cholesterol) is observed in the animals of groups 1 and 2 compared with the control group.

EXAMPLE 2

CNCM I-3741 Strain Growth on Milk

The properties with respect to growth on milk of the CNCM I-3741 strain were tested using the following protocol:

A medium made up of reconstituted skimmed milk (120 g of skimmed milk powder in one liter of distilled water, supplemented with 2 g/l of yeast extract) was inoculated with the CNCM I-3741 strain or, by way of comparison, with the *L. delbrueckii* subspecies *bulgaricus* strain CNCM I-1519 (this strain, which is described in Application EP 0858501, has conventional properties in terms of fermentation).

The fermentative activity of the strains, linked to their growth, is measured by continuously managing the pH of the growth medium.

Figure 3:
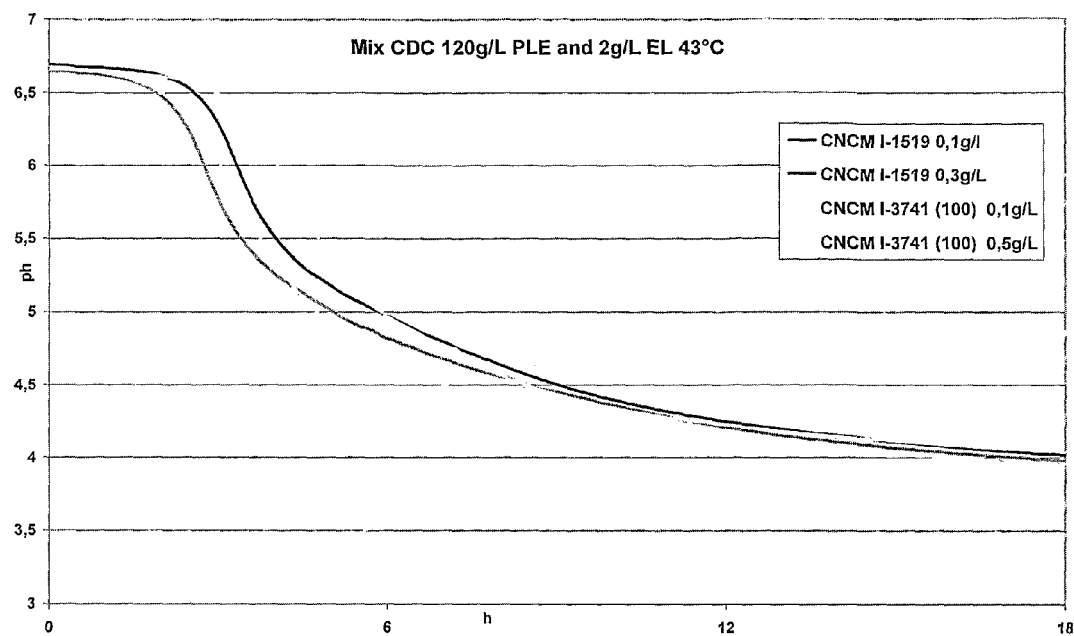

The results are given in FIG. 3.

These results show that the CNCM I-3741 strain is capable of growing efficiently on milk, and that it can therefore be used in the manufacture of fermented milk products.

The invention claimed is:

1. An isolated *Lactobacillus delbrueckii* subspecies *lactis* strain deposited on 6 Apr. 2007 under Accession number I-3741 with the CNCM (Collection Nationale de Cultures de Microorganismes).

2. A lactic ferment composition comprising the isolated *Lactobacillus delbrueckii* subspecies *lactis* strain according to claim 1, combined with one or more other strain(s) of lactic acid bacteria.

3. The lactic ferment composition according to claim 2, wherein said other strain(s) of lactic acid bacteria is (are) chosen from strains belonging to the following species: *Lactobacillus delbrueckii bulgaricus* and *Streptococcus thermophilus*.

4. A fermented product containing the isolated *Lactobacillus delbrueckii* subspecies *lactis* strain of claim 1.

5. A fermented product produced by the isolated *Lactobacillus delbrueckii* subspecies *lactis* strain of claim 1, wherein said fermented product contains said strain.

6. A method of decreasing blood cholesterol levels in a subject in need thereof comprising administering the product of claim 4 to the subject.

7. The method of claim 6 wherein the blood cholesterol is in the LDL form.

* * * * *